United States Patent
Hervieux et al.

(10) Patent No.: US 7,173,437 B2
(45) Date of Patent: Feb. 6, 2007

(54) GARMENT INCORPORATING EMBEDDED PHYSIOLOGICAL SENSORS

(75) Inventors: Paul Hervieux, San Diego, CA (US); Robert Matthews, San Diego, CA (US); Jamison Scott Woodward, Solana Beach, CA (US)

(73) Assignee: Quantum Applied Science and Research, Inc., San Diego, CA (US)

( * ) Notice: Subject to any disclaimer, the term of this patent is extended or adjusted under 35 U.S.C. 154(b) by 0 days.

(21) Appl. No.: 11/148,551

(22) Filed: Jun. 9, 2005

(65) Prior Publication Data

US 2005/0275416 A1    Dec. 15, 2005

Related U.S. Application Data

(60) Provisional application No. 60/578,349, filed on Jun. 10, 2004.

(51) Int. Cl.
*G01R 27/26* (2006.01)
*A61B 5/04* (2006.01)

(52) U.S. Cl. .................. 324/663; 324/690; 600/388

(58) Field of Classification Search ............... 324/663, 324/690; 600/388, 389
See application file for complete search history.

(56) References Cited

U.S. PATENT DOCUMENTS

| | | | |
|---|---|---|---|
| 3,043,291 A | 7/1962 | Nielson | |
| 3,409,007 A * | 11/1968 | Fuller | ............ 600/382 |
| 3,476,104 A | 11/1969 | Davis | |
| 3,500,823 A | 3/1970 | Richardson et al. | |
| 3,565,060 A | 2/1971 | Sipple | |
| 3,620,208 A | 11/1971 | Higley et al. | |
| 3,722,677 A | 3/1973 | Lehnert | |
| 3,744,482 A | 7/1973 | Kaufman et al. | |
| 3,880,146 A | 4/1975 | Everett et al. | |
| 3,882,846 A | 5/1975 | Fletcher et al. | |
| 3,888,240 A | 6/1975 | Reinhold et al. | |
| 3,923,042 A | 12/1975 | Hajdu et al. | |
| 3,954,100 A | 5/1976 | Sem-Jacobsen | |
| 4,248,244 A | 2/1981 | Charnitski et al. | |
| 4,580,576 A | 4/1986 | Blackwood | |
| 4,581,821 A | 4/1986 | Cahalan et al. | |
| 4,602,639 A | 7/1986 | Hoogendoorn et al. | |

(Continued)

FOREIGN PATENT DOCUMENTS

CA    2280996    2/2001

(Continued)

OTHER PUBLICATIONS

"Ultra Low Input Bias Current Instrumentation Amplifier," Burr-Brown Corp., pp. 1-9, 1994.

(Continued)

*Primary Examiner*—Anjan Deb
(74) *Attorney, Agent, or Firm*—Diederiks & Whitelaw, PLC

(57) ABSTRACT

A system for unobtrusively measuring bioelectric signals developed by an individual includes multiple sensors, one or more of which constitutes a capacitive sensor attached to a holding device. The holding device serves as a mounting structure that holds sensors in place within a wearable garment. The holding device and sensors are horizontally and vertically adjustable relative to the garment, while the sensors are pressed against the individual and prevented from undesirable shifting upon movement of the individual.

20 Claims, 6 Drawing Sheets

U.S. PATENT DOCUMENTS

| | | | |
|---|---|---|---|
| 4,669,479 | A | 6/1987 | Dunseath, Jr. |
| 4,688,141 | A | 8/1987 | Bernard et al. |
| 4,698,848 | A | 10/1987 | Buckley |
| 4,709,704 | A | 12/1987 | Lukasiewicz |
| 4,785,237 | A | 11/1988 | Cox |
| 4,801,866 | A | 1/1989 | Wixley |
| 4,889,123 | A | 12/1989 | Lee |
| 5,001,594 | A | 3/1991 | Bobbio |
| 5,015,906 | A | 5/1991 | Cho et al. |
| 5,039,312 | A | 8/1991 | Hollis, Jr. et al. |
| 5,090,643 | A | 2/1992 | Spears |
| 5,119,404 | A | 6/1992 | Aihara |
| 5,169,380 | A * | 12/1992 | Brennan ........................ 600/26 |
| 5,191,891 | A | 3/1993 | Righter |
| 5,229,593 | A | 7/1993 | Cato |
| 5,257,631 | A | 11/1993 | Wilk |
| 5,289,822 | A | 3/1994 | Highe et al. |
| 5,304,941 | A | 4/1994 | Tateishi |
| 5,313,942 | A | 5/1994 | Platzker |
| 5,325,073 | A | 6/1994 | Hasegawa |
| 5,336,999 | A | 8/1994 | Mansfield et al. |
| 5,348,008 | A | 9/1994 | Bornn et al. |
| 5,485,092 | A | 1/1996 | Fortin |
| 5,488,677 | A | 1/1996 | Tokano |
| 5,574,805 | A | 11/1996 | Toba et al. |
| 5,632,280 | A | 5/1997 | Leyde et al. |
| 5,645,527 | A | 7/1997 | Beck |
| 5,650,750 | A | 7/1997 | Leyde et al. |
| 5,670,870 | A | 9/1997 | Muramatsu |
| 5,699,015 | A | 12/1997 | Dotson et al. |
| 5,734,296 | A | 3/1998 | Dotson et al. |
| 5,751,192 | A | 5/1998 | Main |
| 5,781,003 | A | 7/1998 | Kondo |
| 5,795,293 | A | 8/1998 | Carim et al. |
| 5,798,673 | A | 8/1998 | Griffith et al. |
| 5,803,911 | A | 9/1998 | Inukai et al. |
| 5,896,035 | A | 4/1999 | Takahashi |
| 5,947,920 | A | 9/1999 | Beck |
| 5,993,401 | A | 11/1999 | Inbe et al. |
| 6,001,065 | A | 12/1999 | De Vito |
| 6,047,203 | A | 4/2000 | Sackner et al. |
| 6,096,220 | A | 8/2000 | Ohkawa |
| 6,111,466 | A | 8/2000 | Mokhtar et al. |
| 6,134,424 | A | 10/2000 | Nishihori et al. |
| 6,242,911 | B1 | 6/2001 | Maschek |
| 6,254,536 | B1 | 7/2001 | De Vito |
| 6,262,631 | B1 | 7/2001 | Li |
| 6,272,365 | B1 | 8/2001 | Ronkainen et al. |
| 6,289,238 | B1 | 9/2001 | Besson et al. |
| 6,381,482 | B1 | 4/2002 | Jayaraman et al. |
| 6,411,108 | B1 | 6/2002 | Douglas et al. |
| 6,438,413 | B1 | 8/2002 | Taheri |
| 6,472,888 | B2 | 10/2002 | Oguma et al. |
| 6,516,289 | B2 * | 2/2003 | David ........................ 600/384 |
| 6,551,252 | B2 * | 4/2003 | Sackner et al. ............. 600/536 |
| 6,577,893 | B1 | 6/2003 | Besson et al. |
| 6,611,168 | B1 | 8/2003 | Denison et al. |
| 6,656,125 | B2 * | 12/2003 | Misczynski et al. ........ 600/508 |
| 6,686,800 | B2 | 2/2004 | Krupka |
| 6,687,523 | B1 | 2/2004 | Jayaramen et al. |
| 6,755,795 | B2 * | 6/2004 | Marmaropoulos et al. .. 600/587 |
| 6,778,090 | B2 | 8/2004 | Newham |
| 6,783,498 | B2 | 8/2004 | Sackner et al. |
| 6,807,438 | B1 * | 10/2004 | Brun Del Re et al. ...... 600/372 |
| 6,897,788 | B2 | 5/2005 | Khair et al. |
| 6,973,344 | B2 * | 12/2005 | Finneran et al. ............ 600/393 |
| 2001/0056225 | A1 | 12/2001 | De Vito |
| 2002/0038092 | A1 | 3/2002 | Stanaland et al. |
| 2003/0036691 | A1 | 2/2003 | Stanaland et al. |
| 2003/0045804 | A1 | 3/2003 | Brodnick |
| 2003/0132763 | A1 * | 7/2003 | Ellenz ........................ 324/663 |
| 2003/0212319 | A1 * | 11/2003 | Magill ........................ 600/382 |
| 2003/0214408 | A1 | 11/2003 | Grajales et al. |
| 2003/0220553 | A1 | 11/2003 | Axelgaard et al. |
| 2003/0224685 | A1 | 12/2003 | Sharman |
| 2004/0070446 | A1 | 4/2004 | Krupka |
| 2004/0073104 | A1 | 4/2004 | Brun Del Re et al. |
| 2004/0210165 | A1 | 10/2004 | Marmaropoulos et al. |
| 2004/0254435 | A1 | 12/2004 | Mathews et al. |
| 2005/0010096 | A1 | 1/2005 | Blackadar |
| 2005/0054941 | A1 | 3/2005 | Ting et al. |
| 2005/0101873 | A1 | 5/2005 | Misczynski et al. |
| 2005/0113703 | A1 | 5/2005 | Farringdon et al. |
| 2005/0165323 | A1 | 7/2005 | Montgomery et al. |
| 2005/0192488 | A1 | 9/2005 | Bryenton et al. |
| 2005/0234357 | A1 | 10/2005 | Xue et al. |
| 2005/0240087 | A1 | 10/2005 | Keenan et al. |

FOREIGN PATENT DOCUMENTS

| | | |
|---|---|---|
| CA | 2428250 | 11/2003 |
| EP | 282712 | 9/1988 |
| GB | 2353594 | 2/2001 |
| GB | 2388196 | 11/2003 |
| JP | 04-170936 | 6/1992 |
| JP | 07-194563 | 8/1995 |
| WO | WO 93/02616 | 2/1993 |
| WO | 01/016607 | 3/2001 |
| WO | WO 02/071935 | 9/2002 |
| WO | WO 02/093312 | 11/2002 |
| WO | WO 2003/034890 | 5/2003 |
| WO | 03/048789 | 6/2003 |
| WO | 03/079897 | 10/2003 |
| WO | WO 2005/032368 | 4/2005 |

OTHER PUBLICATIONS

Clippingdale et al., "Ultra-High Impedance Voltage Probes and Non-Contact Electrocardiography," Sensors: Technology, Systems and Applications, 1st Edition, IOP Publ. Ltd., pp. 469-472, 1991.

Clippingdale et al., "Non-Invasive Dielectric Measurements with the Scanning Potential Microscope," J. Phys. D: Appl. Phys. Vol. 27, IOP Publ. Ltd., pp. 2426-2430, 1994.

Clippingdale et al., "Ultrahigh Impedance Capacitively Coupled Heart Imaging Array, " Rev. Sci. Instrum., vol. 65, No. 1, pp. 269-270, Jan. 1994.

David et al., "Insulated Electrocardiogram Electrodes," Med. & Biol. Eng., Peter Peregrunis Ltd., vol. 10, pp. 742-751, 1972.

Geddes, L. A., "Electrodes and the Measurement of Bioelectric Events," Wiley-Interscience, pp. 97-106, 1972.

Harland et al., "Electrical Potential Probes—New Directions in the Remote Sensing of the Human Body," Meas. Sci. and Technol., IOP Publ. Ltd., vol. 13, pp. 163-169, 2002.

Harland et al., "Remote Detection of Human Electroencephalograms Using Ultrahigh Input Impedance Electric Potential Sensors," Applied Physics Letters, vol. 81, No. 17, pp. 3284-3286, Oct. 2002.

Harland et al., "High Resolution Ambulatory Electrocardiographic Monitoring Using Wrist-Mounted Electric Potential Sensors," Meas. Sci. and Technol., IOP Publ. Ltd., vol. 14, pp. 923-928, 2003.

Horowitz et al. "The Art of Electronics," 2nd Edition, pp. 96-98, 183-187, 193-207, 209-210, 1989.

Nunez, P. L., "Electric Fields of the Brain: The Neurophysics of EEG," Oxford University Press, New York, pp. 197-198, 1981.

Nunez, P.L. et al., "Spatial-Temporal Structures of Human Alpha Rhythms: Theory, Microcurrent Sources, Multiscale Measurements, and Global Binding of Local Networks," Human Brain Mapping, Wiley-Liss, Inc., vol. 13, pp. 125-164, 2001.

Prance et al., "Electrometer Arrays: Sensing of Spatio-Temporal ELF Fields," Proc. Marelec, London, 3.4, 1997.

Prance et al., "Non-Contact VLSI Imaging Using a Scanning Electric Potential Microscope," Meas. and Sci. Technol., UK, vol. 11, pp. 1229-1235, 1998.

Prance et al., "An Ultra-Low-Noise Electrical-Potential Probe for Human-Body Scanning," Meas. Sci. and Techol., IOP Publ. Ltd., vol. 11, pp. 1-7, 2000.

Richardson, P.C., "The Insulated Electrode: A Pasteless Electrocardiographic Technique," 20th Annual Conference on Engineering in Medicine and Biology, p. 15.7, 1967.

Srebo, R., "Localization of Visually Evoked Cortical Activity in Humans," J. Physiology, Great Britain, vol. 360, pp. 233-246, 1985.

Srinivisan et al., "Spatial Sampling and Filtering of EEG with Spline Laplacians to Estimate Cortical Potentials," Brain Topography, Human Sciences Press, Inc., vol. 8, No. 4, pp. 355-366, 1996.

Foster-Miller Web-Site, http://www.foster-miller.com/t_b t_physiolocial_monitoring.htm.

NewScientist.com Web-Site, http://www.newscientist.com/article.ns?id=dn4255&print=true.

Polar USA Web-Site, http://www.polarusa.com/manufacturers/products/products.asp.

* cited by examiner

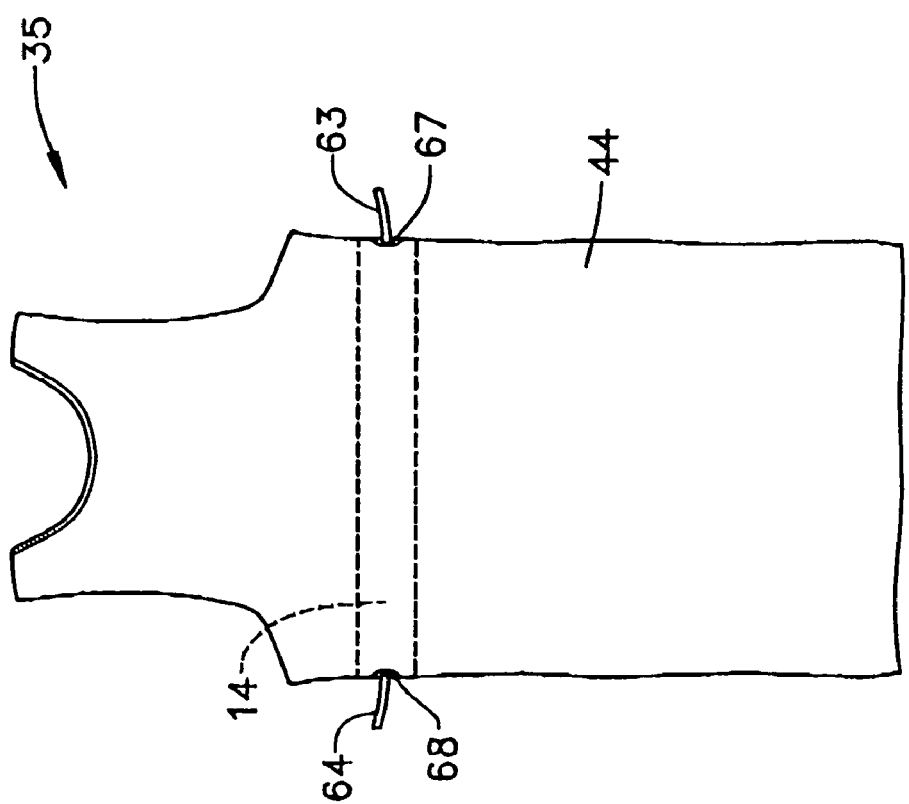
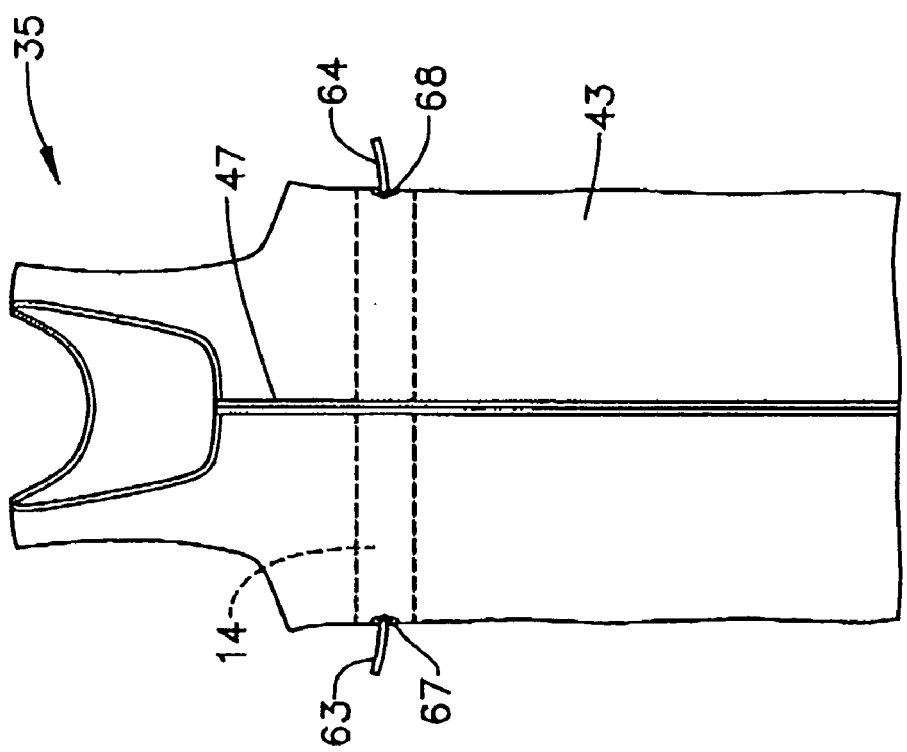

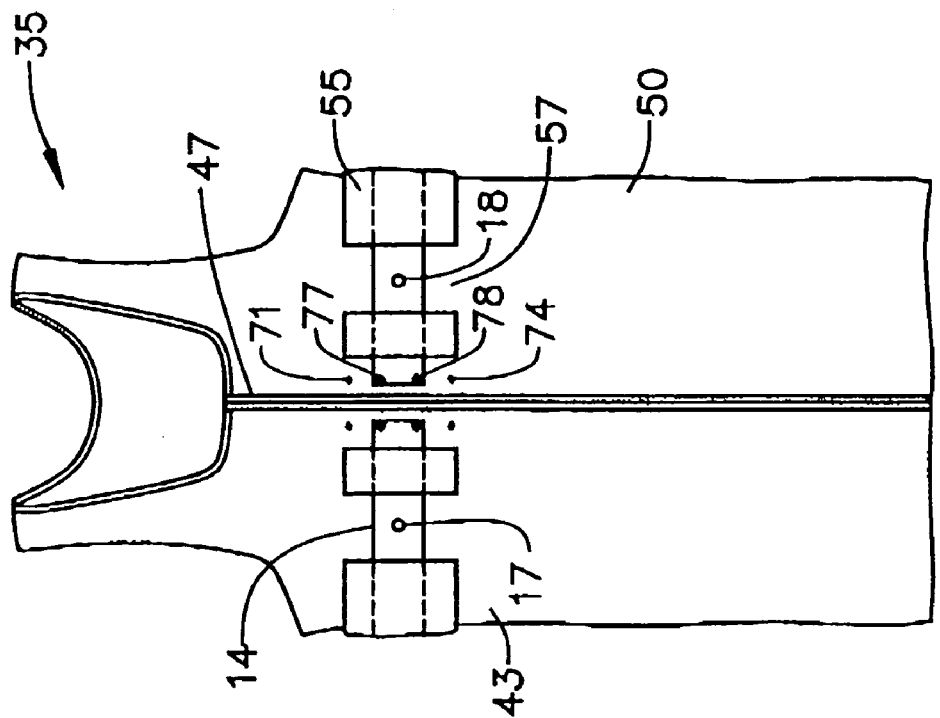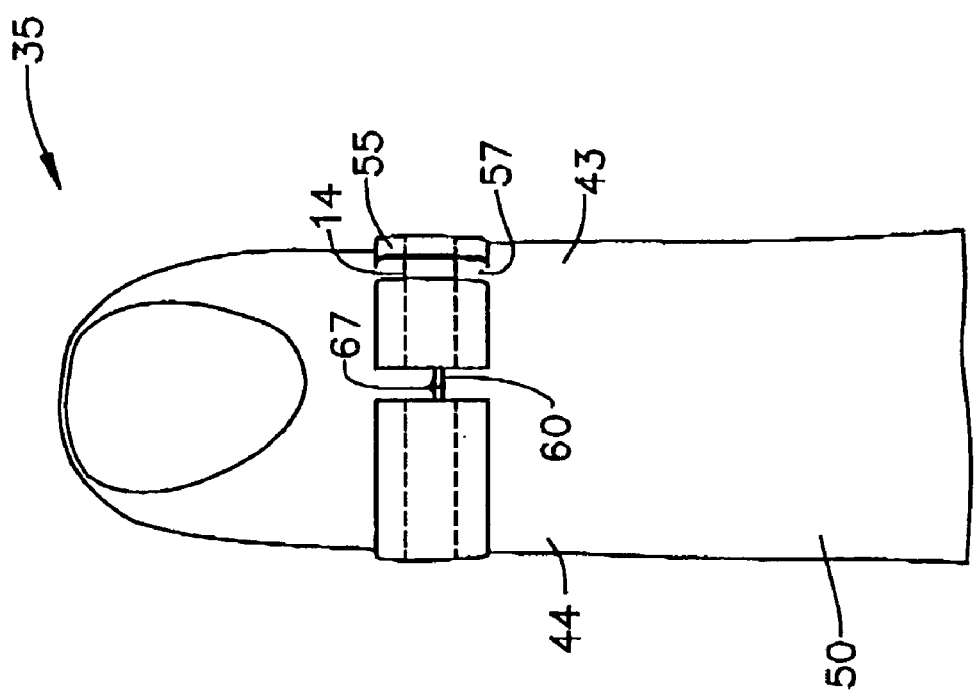

GARMENT INCORPORATING EMBEDDED PHYSIOLOGICAL SENSORS

CROSS-REFERENCE TO RELATED APPLICATIONS

The present invention claims the benefit of U.S. Provisional Patent Application Ser. No. 60/578,349 filed Jun. 10, 2004 entitled "Garment Incorporating Embedded Physiological Sensors."

BACKGROUND OF INVENTION

1. Field of the Invention

The present invention pertains to the art of measuring and monitoring bioelectric signals using sensor systems incorporating at least one capacitive-type electric sensor and, more particularly, to an adjustable garment incorporating embedded psychological sensors.

2. Discussion of the Prior Art

It is widely known that electric potentials and fields are developed in free space from many different sources. For example, organs in the human body, including the heart and brain, produce electric fields throughout the body and in the space outside the body. For a variety of reasons, it is often desirable to measure these electric fields, such as in performing an electrocardiogram (ECG). Indeed, the measurement of bioelectric signals can provide critical information about the physiological status and health of an individual, and is widely used in monitoring, evaluating, diagnosing and caring for patients. Prior methods of measuring electric potentials associated with human or animal subjects employ securing gel-coated electrodes directly to the skin or scalp, or inserting electrodes into the body.

More specifically, electrodes that make a resistive (i.e. Ohmic) electrical contact have been predominantly employed in connection with measuring electric potentials produced by animals and human beings. The disadvantages of such resistive electrodes have been described previously and include discomfort for the patient, the requirement for conducting gels and/or adhesives, difficulty in establishing good electrical contact because of differing physical attributes of the subject (hair, skin properties, etc.), and the degradation in resistive coupling quality over time, among others. These limitations have created a significant barrier to the use of resistive electrodes over extended periods of time and/or when convenience of use is paramount.

Another type of sensor that has been proposed in measuring biopotentials is a capacitive sensor. Early capacitive sensors required a high mutual capacitance to the body, thereby requiring the sensor to also touch the skin of the patient. The electrodes associated with these types of sensors are strongly affected by lift-off from the skin, particularly since the capacitive sensors were not used with conducting gels. As a result, early capacitive sensors were not found to provide any meaningful benefits and were not generally adopted over resistive sensors. However, advances in electronic amplifiers and new circuit techniques have made possible a new class of capacitive sensor that can measure electrical potentials when coupling to a source on the order of 1 pF or less. This capability makes possible the measurement of bioelectric signals with electrodes that do not need a high capacitance to the subject, thereby enabling the electrodes to be used without being in intimate electrical and/or physical contact with the subject. Such capacitive-type sensors and sensing systems have been previously disclosed.

To enhance the measurement of bioelectric signals, there still exists a need for a system that can unobtrusively measure the signals with minimal set-up or preparation time. In addition, there exists a need for a bioelectric signal measuring system that is convenient to use, both for the patient and an operator, such as a nurse, doctor or technician. Furthermore, there exists a need for an effective bioelectric signal measuring system that is adaptable for use by many different sized patients. Specifically, a truly unobtrusive measurement system, which does not require significant preparation or modification for use by different patients, is needed.

SUMMARY OF THE INVENTION

The present invention is directed to a system for unobtrusively measuring bioelectric signals developed by an individual, inclusive of a human or animal. The measurement system enables bioelectric signals to be collected through multiple sensors, one or more of which constitutes a capacitive-type sensor carried by a holding device incorporated into a garment worn by the individual.

In accordance with one embodiment of the invention, the sensors are attached to an elastic band which is held within a shirt, however other garment arrangements can be employed, e.g., belts, hats, headbands and the like. In any case, the band is both horizontally and vertically adjustable within the shirt through the use devices, such as snaps, Velcro, patches, and elastic cord and toggle systems. With this arrangement, an individual, regardless of his or her size, only needs to put on the garment and adjust the position of the band with the simple adjustment devices. The sensors may be attached to the band through sensor carriers, which include a layer of high-traction or anti-slip material for contacting the skin of an individual such that the sensor remains undisturbed by movement of the individual or by adjustment of the holding device. In the alternative, the sensors themselves may carry one or more anti-slip elements. Furthermore, the band may include a foam or inflatable material for pressing the sensors firmly against the individual.

Regardless of the particular implementation, the sensor system of the invention is integrated into a holding device that is incorporated into a garment to be worn by an individual to enable bioelectric signals to be continuously measured in an extremely convenient, unobtrusive and effective way with little or no intervention needed on the part of the individual.

Additional objects, features and advantages of the present invention will become more readily apparent from the following detailed description of preferred embodiments when taken in conjunction with the drawings wherein like reference numerals refer to corresponding parts in the several views.

BRIEF DESCRIPTION OF THE DRAWINGS

FIG. 2 is a front view illustrating the garment of FIG. 1;

FIG. 3 is a back view illustrating the garment of FIGS. 1 and 2;

FIG. 4 is a side view illustrating the garment of FIGS. 1–3;

FIG. 5 is a front view illustrating the garment and sensor system of the invention with vertical adjustment attachment structures;

DETAILED DESCRIPTION OF THE PREFERRED EMBODIMENTS

Figure 1:
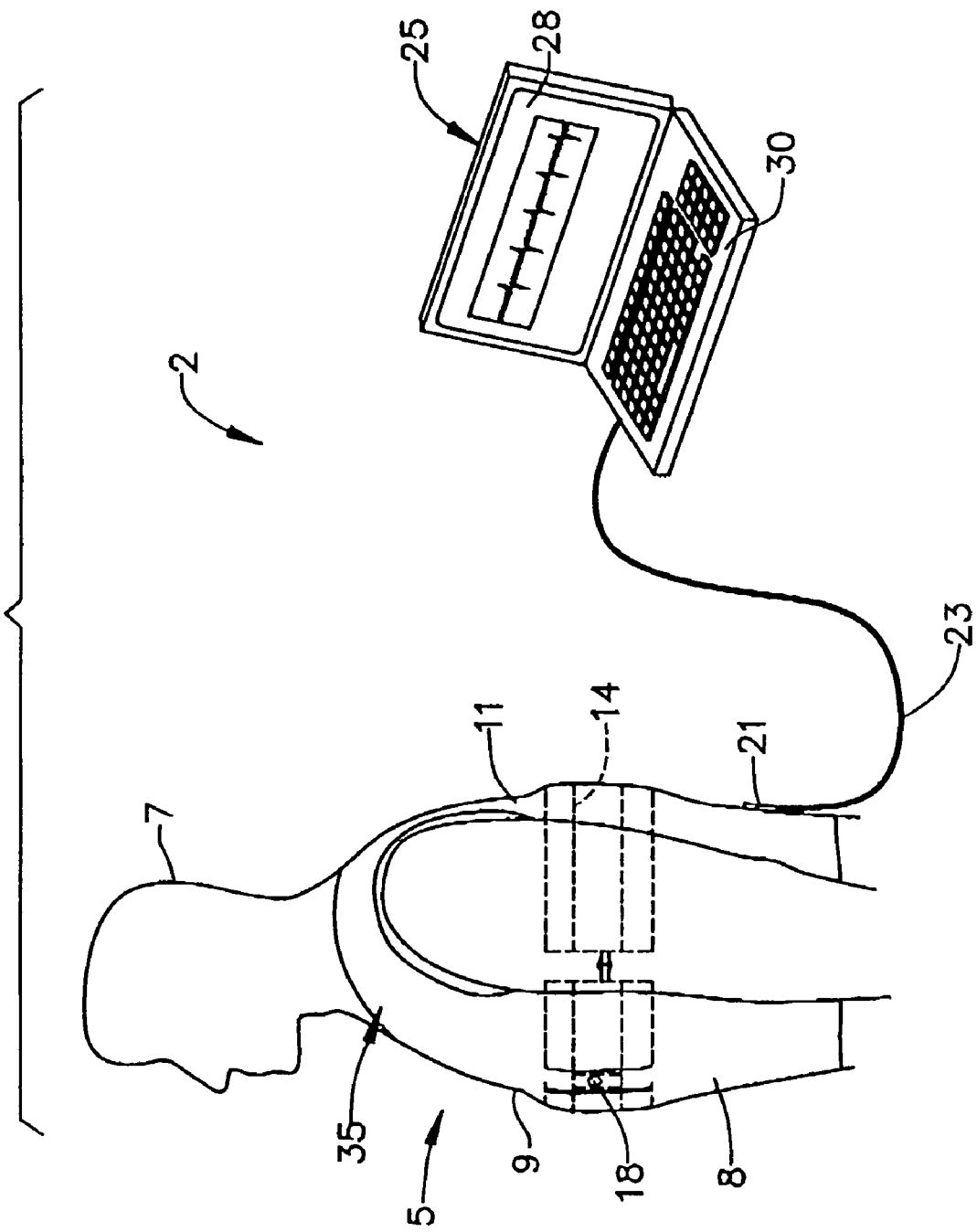
FIG. 1 is a schematic view illustrating a garment incorporating the sensor system of the invention provided on an individual and attached to a control unit.

With initial reference to FIG. 1, a sensor system constructed in accordance with the present invention is generally indicated at 2. In general, sensor system 2 functions to measure biopotentials of an individual 5, such as a medical patient, animal, test subject or the like. As shown, individual 5 includes a head 7 and a torso 8 having a chest 9 and back 11, with torso 8 being surrounded by a holding device which forms part of sensor system 2. In the embodiment shown, the holding device constitutes a band 14. More specifically, sensor system 2 includes band 14 having embedded or otherwise integrated therein at least first and second sensors 17 and 18. In accordance with the invention, at least first sensor 17 constitutes a capacitive-type sensor and, in the most preferred embodiment of the invention, both first and second sensors 17 and 18 constitute capacitive-type sensors.

As shown, each of first and second sensors 17 and 18 is preferably hardwired to a connector 21 and linked through a cable 23 to a remote control unit 25 of sensor system 2. In the embodiment shown, controlling unit 25 constitutes a laptop computer having a display panel 28 and a keyboard 30. The use of sensor system 2 enables individual 5 to wear band 14 whereby a bioelectric field produced by individual 5 can be sensed by first and second sensors 17 and 18, with bioelectric signals being transmitted to control unit 25 for analysis and display purposes. That is, individual 5 will inherently produced time-varying potentials which will be sensed through first and second sensors 17 and 18. As first and second sensors 17 and 18 preferably constitute capacitive-type sensors, no electrically conducting path to the individual 5 is needed. In other words, no flow of real current (electrons) occur between individual 5 and first and second sensors 17 and 18 such that first and second sensors 17 and 18 need not be in physical contact with individual 5. Therefore, the use of capacitive-type sensors enables first and second sensors 17 and 18 to be embedded or otherwise integrated into a holding device worn by individual 5. In this manner, an extremely unobtrusive and convenient sensing system 2 is established which requires very little setup or intervention.

Reference will now be made to FIGS. 1–5 which depict a particular embodiment of the invention. In accordance with this embodiment, sensor system 2 is incorporated into band 14 which is attached to a garment 35. In the embodiment shown, garment 35 constitutes a shirt. However, other types of garments including belts, hats, headbands and other articles worn by an individual, could also be employed. Attached to band 14 are sensors 17 and 18. Although only sensors 17 and 18 are shown, additional sensors may be used. In any case, each sensor 17, 18 constitutes a capacitive-type sensor and includes a capacitive-type electrode having an associated mounting strip (not shown). Each electrode is linked through one or more conductors to connector 21 adapted to be interconnected to control unit 25. Additional information regarding the connection of sensors to the control unit is disclosed co-pending application Ser. No. 10/919,461 entitled "Unobtrusive Measurement System for Bioelectric Signals" and hereby incorporated by reference.

As illustrated by FIGS. 2 and 3, garment 35 may be a sleeveless shirt having a front 43 and a back 44. A zipper 47 extends up front 43 of garment 35 such that individual 5 may easily put on or take off garment 35. As best shown in FIGS. 3 and 5, band 14 is held in position on an inside 50 of garment 35 by a plurality of strips or loops, one of which is indicated at 55, that define respective slots (not labeled) which alternate with a plurality of gaps, one of which is indicated at 57. Preferably, sensors 17 and 18 are positioned on band 14 at one of the plurality of gaps 57, exposing sensors 17 an 18 to individual 5. Band 14 is actually fed through the plurality of slot or sleeve defining strips 55 to limit shifting of band 14 within garment 35. Sensor 17 may be connected to other sensors (not separately labeled) and communicate with control unit 25, such as through cable or cord 23. However, it should be noted that a wireless connection could also be employed. Garment 35 may include a pocket (not shown) for holding a smaller control unit or wireless transmitter (not shown).

In accordance with an aspect of the invention, band 14 is horizontally adjustable or capable of being cinched or otherwise adjusted in combination with garment 35 to accommodate individuals 5 of varying shapes and sizes. To this end, a cord 60 having free ends, two of which are shown at 63 and 64 in FIGS. 2 and 3, is coupled to band 14. Free ends 63 and 64 can be drawn in opposite directions through grommets 67 and 68 and held by a toggle (not shown) to bring band 14 from a first larger circumference to a second smaller circumference, thereby drawing band 14 and sensors 17 and 18 closer to torso 8 of individual 5. Alternatively, other horizontal adjustment or cinching devices may be used to change the circumference of band 14. Some additional adjustment devices include, but are not limited to, Velcro patches, snaps, hook and eyelet fasteners, and plastic loop fasteners. Alternatively, the sensor 17, 18 may have a Velcro patch (not shown) attached thereto such that the sensor 17, 18 may be independently adjustable along band 14.

Figure 6:
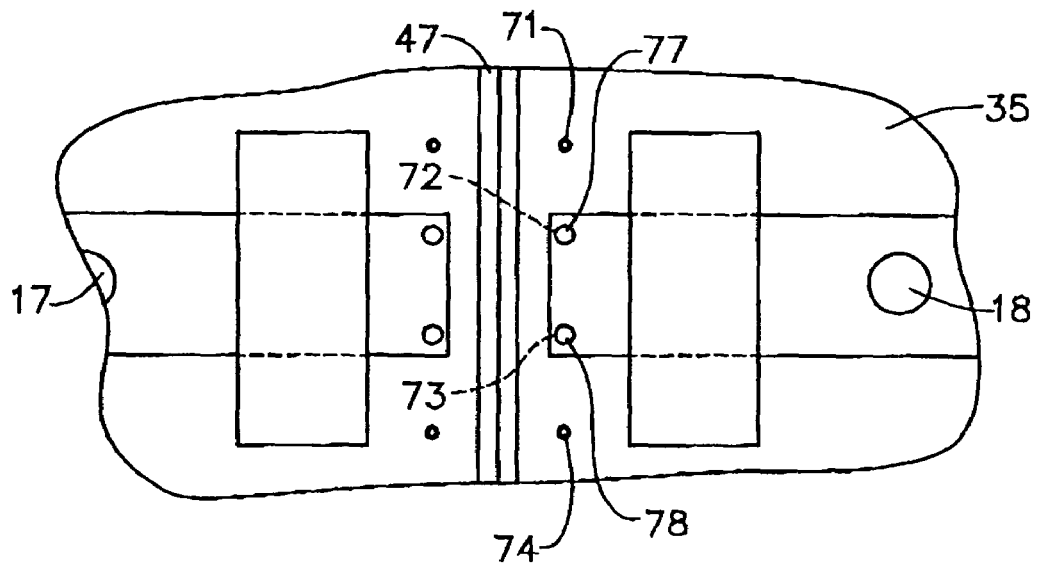
FIG. 6 is an enlarged view of the attachment structures of FIG. 5.
Figure 7:
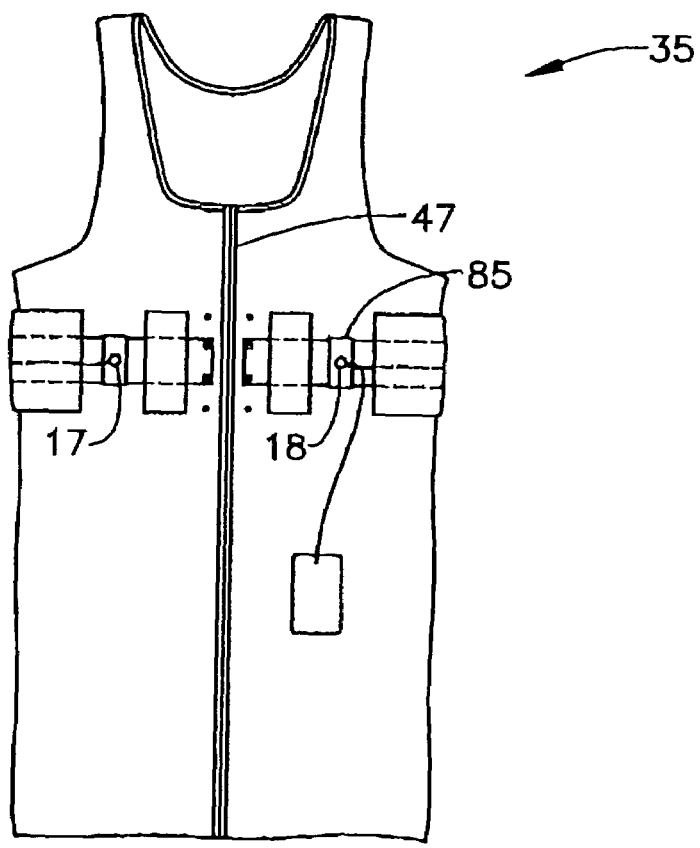
FIG. 7 is a front view illustrating the garment and sensor system of the invention incorporating sensor carriers.

In accordance with another aspect of the invention as best illustrated in FIGS. 5–7, band 14 is also vertically adjustable to accommodate individuals 5 of varying heights or to simply vertically reposition sensors 17 and/or 18. In accordance with a preferred embodiment, vertically spaced apart attachment structures, such as snaps 71–74, are integrated into garment 35 to allow band 14 to be easily moved between different vertical positions. More specifically, in the embodiment shown, band 14 includes snaps 77 and 78 which may be coupled to either snaps 71 and 72, snaps 72 and 73, or snaps 73 and 74, each of which would place band 14 at a different vertical position. Each of FIGS. 5–7 shows belt snaps 77 and 78 fastened to snaps 72 and 73, thereby placing band 14 in an intermediate vertical position. In order to allow individual 5 or other personnel to easily adjust the vertical position of band 14, snaps 71–74 are preferably positioned adjacent to zipper 47 of garment 35. Although band 14 is vertically adjustable through the use of snaps 71–74 in the embodiment shown, other adjustment devices, such as Velcro patches, snaps, hook and eyelet fasteners, plastic loop fasteners or any other attachment or adjustment device, may be used. As described above, sensor 17, 18 may include separate fasteners (not shown) to allow sensor 17, 18 to be independently moved horizontally or vertically on band 14.

Horizontal expansion or contraction of band 14 may cause pulling or dragging of sensor 17, 18 with a lateral force which could cause moving of sensor 17, 18 with respect to torso 8 of individual 5. Movement of sensor 17, 18 generates electrostatic charges, which induces noise artifacts. Noise artifacts are generated by either triboelectric effects between the surface of the electrode (not separately labeled) of sensor 17, 18 and the skin or clothing of individual 5 or by sensor 17, 18 loosing communication with individual 5, such as by tilting, and thus becoming sensitive to free space electric fields.

Figure 8A:
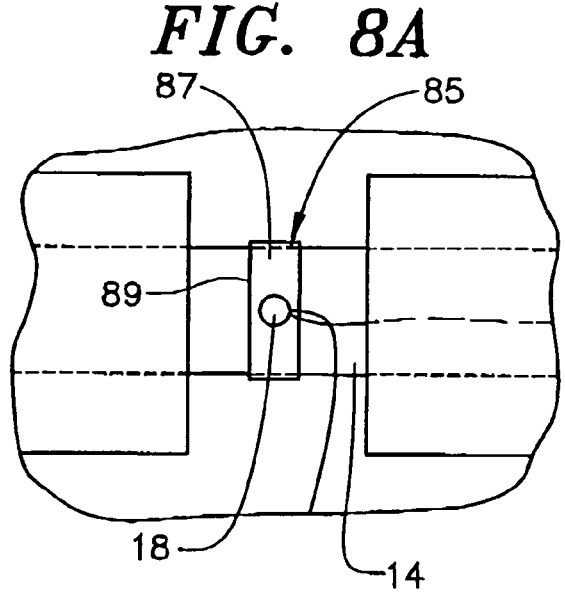
FIG. 8A is an enlarged view of the sensor carrier of FIG. 7.
Figure 8B:
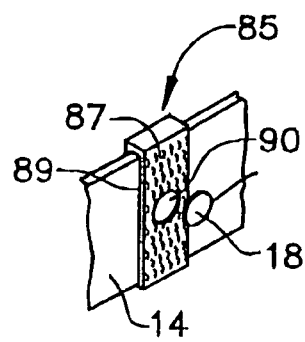
FIG. 8B is a still larger, yet exploded view of the sensor carrier of FIG. 8A.

In order to substantially eliminate noise artifacts generated by movement of sensor 17, 18, a sensor carrier 85 may be used in connection with the sensor system 2 of the invention, as illustrated with reference to sensor 18 in FIGS. 7, 8A and 8B. Sensor carrier 85 includes a first surface 87 to be positioned adjacent individual 5, a second surface (not shown) for facing away from individual 5, and a slot 89 formed therebetween for band 14 to slide through. This arrangement enables sensor carrier 85 to shift along band 14 as needed. That is, garment 35 and band 14 can shift when individual 5 twists, turns, bends or otherwise moves, while sensor carrier 85 can remain substantially stationary. Formed within first surface 87 is a cut-out or recessed portion 90 into which sensor 18 is adapted to fit. Preferably, sensor 18 is frictionally, adhesively or otherwise fixedly secured in cut-out portion 90. Lateral pressure between sensor 18 and the cut-out portion 90 holds sensor 18 in place. Therefore, sensor 18 may be installed or removed from sensor carrier 85 without the use of fasteners or external hardware. First surface 87 is preferably formed from a high-traction material, such as rubber as depicted in FIG. 8B, which has an increased coefficient of friction with the skin or clothing of individual 5. Interior walls (not shown) of sensor carrier 85 are coated with or formed from a material that minimizes the frictional forces between sensor carrier 85 and band 14 and allows relative movement between sensor carrier 85 and band 14. Therefore, the force of sensor carrier 85 and corresponding sensor 17, 18 against individual 5 remains substantially constant and undisturbed by horizontal adjustments of band 14 or through breathing or movement by individual 5. In addition, various types of anti-slide coatings or devices may be applied directly to band 14. The high-traction material could also be provided directly on sensor 17 and/or 18. For instance, this high-traction material can take the form of a ring, pegs of rubber or other structure which will effectively reduce the amount of relative motion between sensor 17, 18 and the skin of individual 5, or an optionally interposed fabric layer. The use of the high-traction material in connection with enhancing the ability of band 14 to move and slide relative to sensor 17, 18 and sensor carrier 85 has been found to advantageously prevent translational motion and frictional forces from being transferred to sensor carrier 85 based on movement of band 14 and enables each sensor 17, 18 to remain essentially fixed relative to the skin of individual 6 in order to minimize any artifact noises in the measurements taken.

Figure 9A:
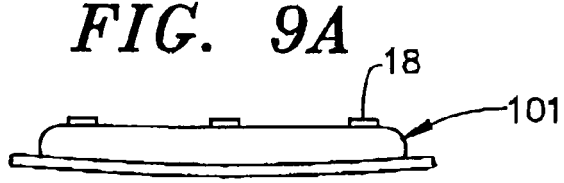
FIGS. 9A is a top view illustrating a foam insert for use with the sensor system of the invention.
Figure 9B:
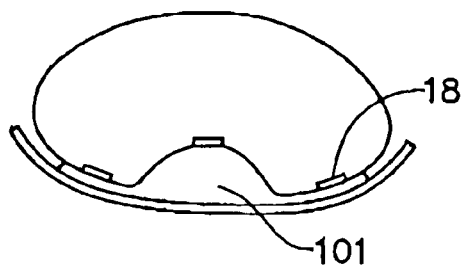
FIG. 9B is another top view illustrating the foam insert of FIG. 9A.
Figure 10A:
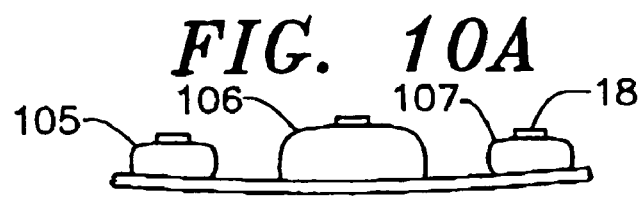
FIG. 10A is a top view illustrating inflatable inserts for use with the sensor system of the invention.
Figure 10B:
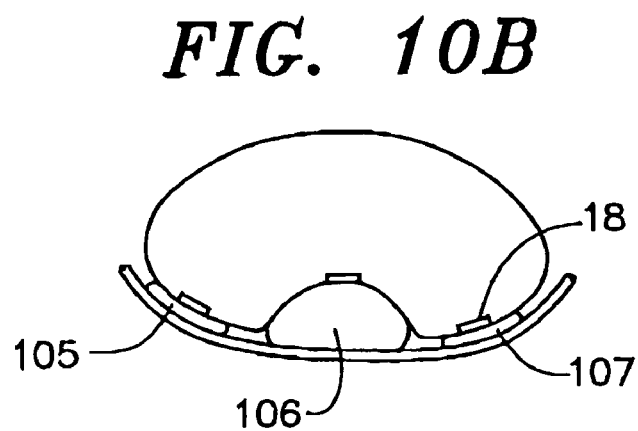
FIG. 10B is another top view illustrating the inflatable inserts of FIG. 10A.
Figure 11:
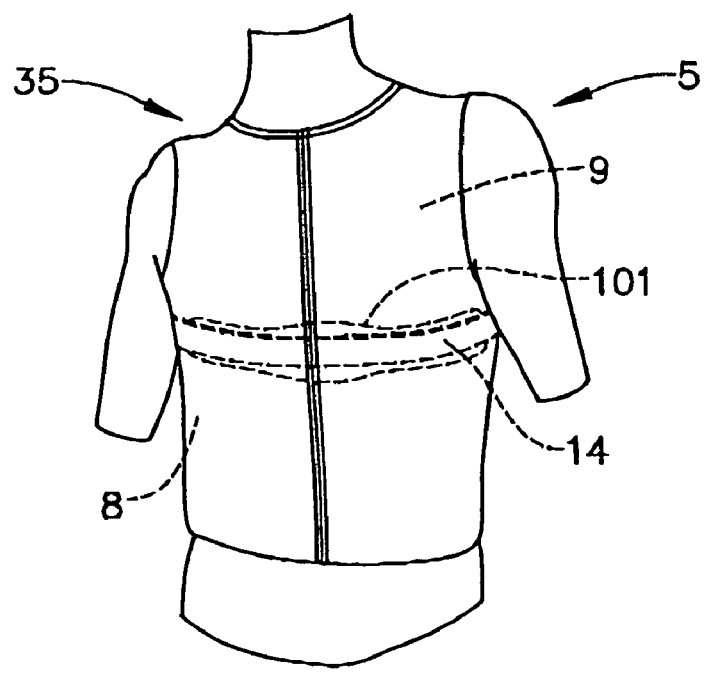
FIG. 11 is a view illustrating the sensor system of the invention incorporating the foam insert of FIGS. 9A and 9B against a torso of an individual.

FIGS. 9A–11 illustrate another aspect of the invention that ensures suitable pressure between sensor 18 and individual 5. Since torso 8 of individual 5 is contoured in a non-uniform manner, band 14 may not create uniform pressure against torso 8. This may cause sensor 18 to move relative to torso 8 in an undesired manner. As shown in FIGS. 9A, 9B and 11, an insert 101 may be used to distribute pressure uniformly behind one or more sensors 18. FIG. 9A illustrates insert 101 in a first position prior to being worn by individual 5. FIGS. 9B and 11 illustrate band 14 and insert 101 as worn by individual 5. Alternatively, multiple inserts 105–107 may be used to distribute pressure behind a respective sensor 18. FIGS. 10A and 10B illustrate band 14 with inserts 105–107 before and during use, respectively. Inserts 101 and 105–107 may be formed from passive foam, dynamic foam, compressible "memory" foam, inflatable air bladders or any other material capable of filling concave voids based on body type and applying positive, substantially perpendicular pressure of the sensor 17, 18 to the individual 5.

Although described with reference to preferred embodiments of the invention, it should be readily understood that various changes and/or modifications can be made to the invention without departing from the spirit thereof. Regardless of the particular implementation, the sensor system of the invention is integrated with a holding device, such as a band or spring member, and a garment, e.g., shirt, belt, hat, headband and the like, to be worn by an individual in a manner which provides a force to hold the sensor to the body of the individual while not transferring translational motions of the individual to the sensor through the holding device in order to enable bioelectric signals to be continuously measured for various applications, including EEG, ECG, EOG and EMG, in an extremely convenient, unobtrusive and efficient manner, with little or no intervention needed on the part of the individual producing the bioelectric field to be measured and with minimal artifact noises. The holding device and garment allow the sensors to be easily adjusted both horizontally and vertically to accommodate individuals of different shapes and sizes. Although only a single band 14 has been described, multiple band segments could be employed, preferably ranging from about 4 inches (approximately 10 cm) to 8 inches (approximately 20 cm) apart. Circumference variations can be readily provided in accordance with the invention. Finally, height adjustments can be a fraction of an inch to six or more inches, e.g., 0.25 inches (approximately 0.6 cm) to 6.5 inches (approximately 16.5 cm). In the overall system, the bioelectric signals can be pre-processed either prior to or by the control unit. For instance, the difference between the outputs of one or more sensors can be taken before transmitting the data or simply prior to further analyzing the data. In any event, the invention is only intended to limited by the scope of the following claims.

We claim:

1. A sensor system for measuring the biopotentials of an individual comprising:
   a garment adapted to be worn by an individual who produces a bioelectric field to be measured;
   a holding device adjustably attached to and supported by said garment, with said holding device being repositionable on the garment; and
   a plurality of electrical sensors integrated into the holding device while permitting relative movement between select ones of the plurality of electrical sensors, at least one of the plurality of electrical sensors being constituted by a capacitive-type electrical sensor, wherein placement of the sensors is controlled by selective adjustment of the holding device relative to the garment and positioning of at least one of the plurality of electrical sensors relative to another one of the plurality of electrical sensors.

2. The sensor system according to claim 1, further comprising: a horizontal adjustment structure for adjusting the holding device from a first circumference to a second circumference, thereby forcing the plurality of sensors against the individual.

3. The sensor system according to claim 1, wherein the holding device constitutes a band adapted to circumscribe a torso of an individual wearing the garment.

4. The sensor system according to claim 3, further comprising: an insert attached to the band for pressing the at least one of the plurality of sensors against the individual.

5. The sensor system according to claim 4, wherein the insert is formed of foam.

6. The sensor system according to claim 4, wherein the insert is inflatable.

7. The sensor system according to claim 1, wherein the garment is selected from the group consisting of a shirt, belt, headband and hat.

8. A sensor system for measuring the biopotentials of an individual comprising:
    a garment adapted to be worn by an individual who produces a bioelectric field to be measured;
    a holding device adjustably attached to said garment;
    a plurality of electrical sensors integrated into the holding device, at least one of the plurality of electrical sensors being constituted by a capacitive-type electrical sensor, wherein placement of the sensors is controlled by adjustment of the holding device; and
    first and second vertically spaced apart attachment structures integrated into the garment, wherein the holding device is adjustable relative to the garment between first and second vertical positions by being selectively attached to either the first or second attachment structures.

9. A sensor system for measuring the biopotentials of an individual comprising:
    a garment adapted to be worn by an individual who produces a bioelectric field to be measured;
    a holding device adjustably attached to said garment;
    a plurality of electrical sensors integrated into the holding device, at least one of the plurality of electrical sensors being constituted by a capacitive-type electrical sensor, wherein placement of the sensors is controlled by adjustment of the holding device; and
    a sensor carrier attached to the holding device for relative sliding movement, said sensor carrier supporting at least one of the plurality of electrical sensors for movement relative to both the holding device and another one of the plurality of electrical sensors.

10. The sensor system according to claim 9, wherein at least one of the sensor carrier and the plurality of electrical sensors is provided with a high-traction material such that the at least one of the plurality of sensors remains substantially undisturbed relative to the individual upon movement of either the individual or the holding device.

11. The sensor system according to claim 9, wherein the sensor carrier includes a cut-out portion for holding the at least one of the plurality of electrical sensors.

12. A method of sensing bioelectric signals from an individual producing a bioelectric field comprising:
    attaching at least one electrical sensor to a sensor carrier, with the at least one sensor being constituted by a capacitive-type electrical sensor;
    mounting the sensor carrier to a holding device;
    providing at least one additional electrical sensor on the holding device;
    attaching the holding device to a garment to be worn by an individual who produces a bioelectric field to be measured, with the sensor carrier being selectively movable relative to the at least one additional electrical sensor, the holding device and the garment;
    placing the garment on the individual;
    positioning the at least one sensor against the individual in a desired location; and
    sensing bioelectric signals from the individual.

13. The method of claim 12, wherein positioning the at least one sensor against the individual includes providing a force to hold the at least one sensor against the individual.

14. The method of claim 13, wherein positioning the at least one sensor against the individual includes horizontally adjusting the holding device to fit the individual.

15. The method of claim 13, wherein positioning the at least one sensor against the individual includes substantially preventing motions of the holding device from being translated to the sensor carrier and the at least one sensor.

16. The method of claim 15, wherein preventing motions of the holding device from being translated includes slidably attaching the sensor carrier to the holding device with a low frictional surface material therebetween.

17. The method of claim 15, wherein preventing motions of the holding device from being translated includes providing a high-traction material on at least one of the sensor carrier and the at least one sensor such that the at least one sensor remains substantially undisturbed upon movement of the individual or adjustment of the holding device.

18. The method of claim 12, wherein positioning the at least one sensor against the individual includes pressing the at least one sensor against the individual with an insert.

19. The method of claim 18, further comprising: inflating the insert.

20. A method of sensing bioelectric signals from an individual producing a bioelectric field comprising:
    attaching at least one electrical sensor to a sensor carrier, with the at least one sensor being constituted by a capacitive-type electrical sensor;
    mounting the sensor carrier to a holding device;
    attaching the holding device to a garment to be worn by an individual who produces a bioelectric field to be measured, with the sensor carrier being movable relative to at least one of the holding device and the garment;
    placing the garment on the individual;
    positioning the at least one sensor against the individual in a desired location by vertically adjusting the holding device relative to the garment, wherein placement of the at least one sensor is controlled by adjustment of the holding device; and
    sensing bioelectric signals from the individual.

* * * * *